(12) United States Patent
Carlucci et al.

(10) Patent No.: US 8,231,893 B2
(45) Date of Patent: Jul. 31, 2012

(54) MULTICOMPONENT MATERIAL COMPRISING CHITOSAN

(75) Inventors: Giovanni Carlucci, Chieti (IT); Daniela Meo, Salerno (IT); Maurizio Tamburro, Sambuceto San Giovanni Teatino (CH) (IT); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 1149 days.

(21) Appl. No.: 11/471,929

(22) Filed: Jun. 21, 2006

(65) Prior Publication Data
US 2007/0009581 A1 Jan. 11, 2007

(30) Foreign Application Priority Data
Jun. 22, 2005 (EP) .................................... 05013435

(51) Int. Cl.
*A61K 9/70* (2006.01)
*A61L 9/00* (2006.01)
(52) U.S. Cl. ..................................... 424/443; 424/76.1
(58) Field of Classification Search ........................ None
See application file for complete search history.

(56) References Cited

U.S. PATENT DOCUMENTS

| 6,197,322 B1 * | 3/2001 | Dutkiewicz et al. .......... 424/412 |
| 7,291,674 B2 * | 11/2007 | Kang et al. ................... 525/54.1 |
| 2004/0166307 A1 | 8/2004 | Tamburro et al. |
| 2004/0167487 A1 | 8/2004 | Tamburro et al. |
| 2005/0003725 A1 | 1/2005 | Hill et al. |
| 2005/0154364 A1 | 7/2005 | Carlucci et al. |
| 2006/0171999 A1 * | 8/2006 | Xin et al. ...................... 424/443 |

FOREIGN PATENT DOCUMENTS

| EP | 0 393 825 B1 | 6/1994 |
| EP | 0 437 816 B1 | 7/1995 |
| WO | WO 03/018073 A2 | 3/2003 |
| WO | WO 03/018074 A2 | 3/2003 |

OTHER PUBLICATIONS

European Search Report dated Dec. 1, 2005.

* cited by examiner

*Primary Examiner* — David J Blanchard
*Assistant Examiner* — Tigabu Kassa
(74) *Attorney, Agent, or Firm* — Andres E. Velarde

(57) ABSTRACT

A multicomponent material, which is comprised of chitosan material being coated onto an inert carrier material. The multicomponent material can be incorporated into an absorbent structure. In one aspect of the invention, the multicomponent material can be incorporated throughout the thickness of an absorbent structure. Absorbent articles comprising the multicomponent material are also provided.

14 Claims, No Drawings

MULTICOMPONENT MATERIAL COMPRISING CHITOSAN

FIELD OF THE INVENTION

The present invention relates to the field of absorbent articles for personal hygiene, such as sanitary napkins, pantiliners, and incontinence pads. More particularly, the present invention relates to a multicomponent material, which is comprised of chitosan material coated onto an inert carrier material.

BACKGROUND OF THE INVENTION

The use of chitosan in absorbent articles for personal hygiene has been disclosed in the literature for various purposes. Such exemplary applications of chitosan are, e.g., absorption of saline fluids like urine or absorption of blood or menses. Further applications of chitosan have been identified in the field of odor control.

Typically, absorbent articles of personal hygiene, such as sanitary napkins, panty liners, diapers, incontinence articles or tampons, comprise an absorbent element for absorbing and retaining fluids. Such absorbent elements are usually constructed of fibers. It has proven most useful to apply the chitosan material in or adjacent to these absorbent elements for maximum functionality. Conventionally, such application of chitosan material to fibrous substrates is facilitated by spraying. Exemplary processes are disclosed in EP-A-1418953 and EP-A-1425049. Both references teach spraying of a solution of chitosan material with a certain droplet size onto the fibrous substrate. By this, a very defined particle size and a very defined manner of application can be achieved. On the other hand, by the nature of spraying processes, the application will always be superficial, i.e., on the surface of the fibrous substrates.

There are applications where it is beneficial to incorporate chitosan material into the interior of a fibrous substrate. Further, spraying applications require a high complexity in terms of equipment and control of process variables.

There is thus a need for providing an alternative for convenient application of chitosan material into fibrous structures.

SUMMARY OF THE INVENTION

The invention is directed to a multicomponent material including an inert carrier material wherein chitosan material is coated onto the inert carrier material. In one aspect of the invention, the multicomponent material can be incorporated into an absorbent structure. In one aspect of the invention, the multicomponent material can be incorporated throughout the thickness of an absorbent structure. An absorbent article comprising an absorbent structure is also provided.

DETAILED DESCRIPTION OF THE INVENTION

Inert Carrier Material

"Inert" as used herein refers to materials that do not substantially react with water. Further, inert materials herein do not substantially swell, gelify, lose integrity or dissolve when exposed to water.

"Particulate material" or "particles" herein refers to materials, which are present as a multiplicity of discrete particles. Such inert carrier material particles can be of any desired shape, e.g., spherical or semi-spherical, cubic, rod-like, polyhedral, etc. Suitable particle shapes herein can be granules, beads, and the like. Shapes having a large greatest dimension/smallest dimension ratio, like needles and flakes, are also contemplated for use herein. The inert carrier material particles herein can be used in the form of discrete particles. The size of the inert carrier material particles may vary over a wide range. For reason of industrial hygiene, average particle sizes smaller than about 30 µm are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. In one embodiment, inert carrier material particles, substantially all of which have a particle size of from about 50 µm to about 1500 µm; from about 100 to about 1000 µm; or from about 100 to about 600 µm, can be used. "Particle Size" as used herein means the weighted average of the smallest dimension of the individual particles.

Suitable inert carrier material particles herein are, for instance, silicon oxide $SiO_2$, commonly referred to as sand. Suitable $SiO_2$ material is marketed by Sibelco under the trade name of Silica Sand of Mol M31, M32, M34. Other examples are granules of polymeric material, such as polyolefins like polyethylene or polypropylene, or glass beads. In other embodiments, particles made of porous material, like zeolites, can be used. Such porous materials have cavities into which the chitosan material can enter. These materials are inert towards water and other body fluids they may be exposed to in an absorbent article for personal hygiene.

In other embodiments of the present invention the inert carrier material is present as fibers. In further embodiments of the present invention the inert carrier material is present as a mixture of fibers and particles.

Chitosan Material

The inert carrier material can be provided with a coating of chitosan material on at least part of the surface. In one embodiment, the chitosan material covers the entire surface of the inert carrier material. In another embodiment, the chitosan material does not cover more than about 70% of the total surface of the inert carrier material. In other embodiments, the chitosan material is also present in the interior of the inert carrier material, such as when coating porous inert carrier materials like zeolite particles or when forming agglomerates from individual particles or fibers.

The chitosan material can have any pH value. In one embodiment, the chitosan material is acidic. In one embodiment, the chitosan material can have a pH value of from about 3 to about 6. "Acidic" as used herein refers to the property of a material to establish a pH lower than 7 in an aqueous solution.

By "chitosan material", it is meant herein chitosans, modified chitosans, crosslinked chitosans, chitosan salts or mixtures thereof. Chitosan is a partially or fully deacetylated form of chitin, a naturally occurring polysaccharide. Indeed, chitosan is an aminopolysaccharide usually prepared by deacetylation of chitin (poly-beta(1,4)-N-acetyl-D-glucosamine).

Chitosan is not a single, definite chemical entity but varies in composition depending on the conditions of manufacture. It may be equally defined as chitin sufficiently deacetylated to form soluble amine salts. Chitosan is the beta-(1,4)-polysaccharide of D-glucosamine and is structurally similar to cellulose, except that the C-2 hydroxyl group in cellulose is substituted with a primary amine group in chitosan. The large number of free amine groups makes chitosan a polymeric weak base. Solutions of chitosan are generally highly viscous, resembling those of natural gums.

In one embodiment, the chitosan used herein can be in relatively pure form. Methods for the manufacture of pure chitosan are well known. Generally, chitin is milled into a powder and demineralised with an organic acid such as acetic acid. Proteins and lipids are then removed by treatment with a base, such as sodium hydroxide, followed by chitin deacetylation by treatment with concentrated base, such as 40 percent sodium hydroxide. The chitosan formed is washed with water until the desired pH is reached.

The properties of chitosan relate to its polyelectrolyte and polymeric carbohydrate character. Thus, it is generally insoluble in water, in alkaline solutions at pH levels above about 7, or in hydrophobic organic solvents. It generally dissolves readily in dilute aqueous solutions of organic acids such as formic, acetic, tartaric, glycolic, lactic and citric acids and also in dilute aqueous solutions of mineral acids, except, for example, sulphuric acid. In general, the amount of acid required to dissolve chitosan is approximately stoichiometric with the amino groups. Since the $pK_a$ for the amino groups present in chitosan is between 6.0 and 7.0, they can be protonated in very dilute acids or even close to neutral conditions, rendering a cationic nature to this biopolymer. This cationic nature is the basis of many of the benefits of chitosan. Indeed, chitosan material can be considered as a linear polyelectrolyte with a high charge density that can interact with negatively charged surfaces such as, for example, proteins (e.g., by interfering with the proteinic wall construction of microorganisms, thereby acting as an antimicrobial agent and/or by reacting with the proteins present in bodily fluid, like menses, thereby acting as a gelifying agent for such fluid).

Without wishing to be bound by any theory, it is believed that chitosan material retains electrolyte-containing fluids like body fluids by multiple mechanisms. One mechanism is conventional absorption by incorporation of the water dipole molecules into the structure. As the positively charged quaternary ammonium groups are distracting each other, molecular cavities exist in which water molecules can penetrate. By the penetration of dipole molecules, like water, these cavities can be widened by swelling and thereby generating even more space for further water molecules. This mechanism can be continued until the limits of molecular tension are reached.

The second mechanism of binding electrolyte-containing fluids like body fluids by chitosan material is gelification. Chitosan material acts electrostatically on nearby negatively charged molecules and thereby holds them in its circumference. The positively charged cationic groups (e.g., quaternary ammonium groups) of the chitosan material will interact with negatively charged anionic function-bearing molecules present in bodily fluids, like, for example, the carboxylic groups of proteins or cell membrane of red blood cells. This will result in the formation of a three-dimensional network between the chitosan material and such molecules with anionic groups (gelification of the bodily fluids). This gelification will further entrap other molecules present in body fluids (like lipids, acids). Due to the gelification properties of the chitosan material with respect to electrolyte-containing fluids, a liquid barrier is generated when the chitosan material is wetted by such fluids.

Chitosan materials for use herein can have an average degree of deacetylation (D.A.) of more than about 70%, such as, e.g., from about 80% to about 100%. The degree of deacetylation refers to the percentage of the amine groups that are deacetylated. This characteristic is directly related to the hydrogen bonding existing in this biopolymer, affecting its structure, solubility and ultimately its reactivity. The degree of deacetylation can be determined by, e.g., titration, dye adsorption, UV/vis, IR and NMR spectroscopy. The degree of deacetylation will influence the cationic properties of chitosan. By increasing the degree of deacetylation, the cationic character of the chitosan material can increase and thus also its gelifying abilities.

Suitable chitosan materials for use herein include substantially water-soluble chitosan. As used herein, a material will be considered water-soluble when it substantially dissolves in excess water to form a clear and stable solution, thereby losing its initially particulate form and becoming essentially molecularly dispersed throughout the water solution. Chitosan materials for use herein are water soluble, i.e., at least about 1 gram and at least about 3 grams of the chitosan materials are soluble in 100 grams of water at 25° C. and one atmosphere. By "solubility" of a given compound, it is to be understood herein as the amount of said compound solubilised in deionised water at 25° C. and one atmosphere in absence of a precipitate. Generally, the water-soluble chitosan materials will be free from a higher degree of crosslinking, as crosslinking tends to render the chitosan materials water insoluble.

Chitosan materials may generally have a wide range of molecular weights. Chitosan materials with a wide range of molecular weights are suitable for use in the present invention. Typically, chitosan materials for use herein have a molecular weight ranging from about 1,000 to about 10,000,000 grams per gram moles or from about 2,000 to about 1,000,000 grams per gram moles. Molecular weight means average molecular weight. Methods for determining the average molecular weight of chitosan materials are known to those skilled in the art. Typical methods include, for example, light scattering, intrinsic viscosity and gel permeation chromatography. It is generally most convenient to express the molecular weight of a chitosan material in terms of its viscosity in a 1.0 weight percent aqueous solution at 25° C. with a Brookfield viscometer. It is common to indirectly measure the viscosity of the chitosan material by measuring the viscosity of a corresponding chitosan salt, such as by using a 1.0 weight percent acetic acid aqueous solution. Chitosan materials suitable for use in the present invention will suitably have a viscosity in a 1.0 weight-% aqueous solution at 25° C. of from about 10 mPa·s (10 centipoise) to about 100,000 mPa·s (100,000 centipoise); from about 30 mPa·s (30 centipoise) to about 10,000 mPa·s (10,000 centipoise); or about 7000 mPa·s (7000 centipoise).

The pH of the chitosan materials depends on their preparation. Chitosan materials for use herein have an acidic pH, typically in the range of about 3 to about 7, such as, e.g., about 5. By pH of the chitosan material, it is meant herein the pH of a 1% chitosan material solution (1 gram of chitosan material dissolved in 100 grams of distilled water) measured by a pH-meter. By using a more acidic pH, the cationic character of the chitosan materials will be increased and thus their gelifying abilities. However, too high acidity is detrimental to skin safety. Thus, in one embodiment, chitosan materials with a pH of about 5 are used, thereby delivering the best compromise between fluid handling properties on one side and skin compatibility on the other side.

Suitable chitosan materials for use herein include chitosan salts, such as, e.g., water-soluble chitosan salts. A variety of acids can be used for forming chitosan salts. In one embodiment, suitable acids for use are soluble in water or partially soluble in water, are sufficiently acidic to form the ammonium salt of chitosan and yet not sufficiently acidic to cause hydrolysis of chitosan, and are present in an amount sufficient to protonate the reactive sites of chitosan.

Suitable acids can be represented by the formula:

R—(COOH)$_n$ wherein n has a value of 1 to 3 and R represents a mono- or divalent organic radical composed of carbon, hydrogen and optionally at least one of oxygen, nitrogen and sulphur or simply R is a hydrogen atom. In one embodiment, the acids are the mono- and dicarboxylic acids composed of carbon, hydrogen, oxygen and nitrogen (also called hereinafter amino acids). Such acids are biologically acceptable for use against or in proximity to the human body. Illustrative acids, in addition to those previously mentioned, include, among others, citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, 2-pyrrolidone-5-carboylic acid, salyicilic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid and thioglycolic acid. Any chitosan salts formed from the reaction of chitosan with any of these acids or any other suitable acid are suitable for use herein.

Examples of chitosan salts formed with an inorganic acid include, but are not limited to, chitosan hydrochloride, chitosan hydrobromide, chitosan phosphate, chitosan sulphonate, chitosan chlorosulphonate, chitosan chloroacetate and mixtures thereof. Examples of chitosan salts formed with an organic acid include, but are not limited to, chitosan formate, chitosan acetate, chitosan lactate, chitosan glycolate, chitosan malonate, chitosan epoxysuccinate, chitosan benzoate, chitosan adipate, chitosan citrate, chitosan salicylate, chitosan propionate, chitosan nitrilotriacetate, chitosan itaconate, chitosan hydroxyacetate, chitosan butyrate, chitosan isobutyrate, chitosan acrylate and mixtures thereof. It is also suitable to form a chitosan salt using a mixture of acids including, for example, both inorganic and organic acids.

In one embodiment, chitosan salts for use herein are those formed by the reaction of chitosan with an amino acid. Amino acids are molecules containing both an acidic and amino functional group. The use of amino acids is desirable as those chitosan amino salts have higher skin compatibility. Indeed, most of the amino acids are naturally present on the skin. Chitosan salts of pyrrolidone carboxylic acid are effective moisturizing agents and are non-irritating to skin. Amino acids for use herein include both linear and/or cyclo amino acids. Examples of amino acids for use herein include, but are not limited to, alanine, valine, leucine, isoleucine, proline, phenylalanine, tryptophan, methionine, glycine, serine, cysteine, tyrosine, asparagine, glutamine, aspartic acid, glutamic acid, lysine, arginine, histidine, hydroxyproline, threonine, and the like. An example of a cyclic amino acid is pyrrolidone carboxylic acid, which is a carboxylic acid of pyrrolidin-2-one as per following formula:

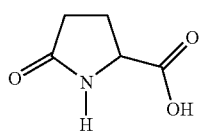

Other chitosan materials suitable for use herein include cross-linked chitosans with a low degree of cross-linkage and modified chitosans. Suitable crosslinking agents for use herein are organic compounds having at least two functional groups or functionalities capable of reacting with active groups located on the chitosan materials. Examples of such active groups include, but are not limited to, carboxylic acid (—COOH), amino (—NH$_2$), or hydroxyl (—OH) groups. Examples of such suitable crosslinking agents include, but are not limited to, diamines, polyamines, diols, polyols, dicarboxylic acids, polycarboxylic acids, aminocarboxylic acids, aminopolycarboxylic acids, polyoxides and the like. One way to introduce a crosslinking agent with the chitosan material solution is to mix the crosslinking agent with chitosan during preparation of the solution. Another suitable crosslinking agent comprises a metal ion with more than two positive charges, such as $Ca^{2+}$, $Al^{3+}$, $Fe^{3+}$, $Ce^{3+}$, $Ce^{4+}$, $Ti^{4+}$, $Zr^{4+}$ and $Cr^{3+}$. Since the cations on chitosan possess antimicrobial properties, in one embodiment a crosslinking agent reacting to the cations is not used, unless no alternative crosslinking agent is available.

Suitable chitosan material is commercially available from numerous vendors. Exemplary commercially available chitosan materials are those available from for example the Vanson Company. In one embodiment, the chitosan salt for use herein is chitosan pyrrolidone carboxylate (also called chitosonium pyrrolidone carboxylate), which has a degree of deacetylation of more than about 85%, a water solubility of about 1% (1 gram is soluble in 100 grams of distilled water at 25° C. and one atmosphere) and a pH of about 5. Chitosonium pyrrolidone carboxylate is commercially available under the name Kytamer® PC from Amerchol Corporation. Another exemplary chitosan salt for use herein is chitosan lactate, the chitosan salt of lactic acid.

In one embodiment, the chitosan material is coated onto the inert carrier material at a thickness of from about 1 to about 100 μm or from about 5 to about 30. Further, in one embodiment, the weight ratio of the inert carrier material to the chitosan material is from about 99:1 to about 1:99, or from about 95:5 to about 30:70.

Coating of the Chitosan Material onto the Inert Carrier Material

The coating of the inert carrier material with chitosan material may be facilitated by any known coating method, for example, by mixing or dispersing the inert carrier material in a solution or dispersion of the chitosan material; by spraying the chitosan material solution or dispersion onto the inert carrier material; by introducing the chitosan material dispersion or solution and the inert carrier material in a fluidised bed or Wurster coater; by agglomerating the chitosan material solution or dispersion and the inert carrier material; by dip-coating the inert carrier material in the chitosan material dispersion or solution. Useful fluidized bed reactors include, for example, the fluidized or suspended bed coaters familiar in the pharmaceutical industry. In one embodiment, the coating is facilitated by the Wurster process known to those skilled in the art. Other suitable mixers include for example twin drum mixers, so called "Zig-Zag" mixers, plough-share mixers, such as Lödige mixers, cone screw mixers, or perpendicularly cylindrical mixers having coaxially rotating blades. Examples of coating processes are, for example, described in U.S. Pat. Nos. 5,840,329 and 6,387,495.

Absorbent Structure and Absorbent Article Containing the Same

The term "absorbent structure" is used herein to describe absorbent webs suitable for use in absorbent articles. The absorbent structure comprises two surfaces aligned substantially opposite to each other. The first and the second surface are spaced apart from each other by the thickness dimension of the absorbent structure. The absorbent structure comprises the multicomponent material of the present invention. The absorbent structure according to the present invention can be used as absorbent core or so-called secondary topsheet or secondary backsheet in absorbent articles. The absorbent structure typically has significant internal void space in the form of pores, holes, apertures, interstitial space between fibers and the like. Examples of absorbent structures for use in the present invention are fibrous webs, such as nonwovens or fabrics, comprising natural or synthetic fibers or mixtures thereof, or apertured polymeric films or foam materials. Indeed, the absorbent structure according to the present invention can be made of any of a variety of fibers, including a blend or admixture. The fibers may be cellulosic, modified cellulosic, or hydrophilic synthetic and include such fibers as wood pulp, rayon, cotton, cellulose acetate, polyester, nylon and the like.

The absorbent structure can be made according to any suitable method known for this purpose in the art. Fibrous absorbent structures according to the present invention can be made by appropriate processes such as dry laying and in particular air laying, melt blowing or spunbonding. Film-like or foam-like absorbent structures according to the present invention are made by processes suitable for such purposes.

In one embodiment, absorbent structures for use herein are hydrophilic fibrous webs. As used herein, "hydrophilic" refers to a material having a contact angle of water in air of less than about 90 degrees, whereas the term "hydrophobic" herein refers to a material having a contact angle of water in air of about 90 degrees or greater. An absorbent structure comprising hydrophilic fibers, like, for example, cellulosic fibers, such as wood pulp fibers, is useful in such products as sanitary napkins, disposable diapers or wipes, because the hydrophilic fibers are liquid absorbent and therefore enhance the overall absorbency of the absorbent structure. Absorbent structures for use herein can be made of a blend of cellulosic and hydrophilic synthetic fibers, for example, comprising about 65% to about 95% by weight of cellulosic fibers and up to about 20% by weight of the hydrophilic synthetic fibers. The hydrophilic synthetic fibers, which can be provided in any length including staple length, can improve the strength of the absorbent structure. Hydrophobic fibers or films, such as fibers or films made of polyethylene or polypropylene, may also be used in the absorbent structure herein provided they are treated by, e.g., surfactants to make them hydrophilic, in order not to decrease the absorbent capacity of the absorbent structure. In other embodiments, the absorbent structure is mainly made of foam material, into which the multicomponent material is distributed.

The absorbent structure of the present invention can be comprised of one layer only. Alternatively, the absorbent structure herein can also be comprised of multiple layers. In one embodiment, the absorbent structure herein also comprises superabsorbent material for absorbing aqueous body fluids. Such superabsorbent materials are well-known in the art, such as, e.g., polyacrylates or hydroxymethylcellulose.

The absorbent structure according to the present invention can be described as having an extension in all of the x, y and z-dimensions in an orthogonal Cartesian system. The multicomponent material is in one embodiment relatively evenly distributed throughout the absorbent structure, thus throughout its whole extension across in said x, y and z-dimension. In other embodiments herein, the multicomponent material of the present invention is not evenly distributed in the absorbent structure but concentrated in certain regions of it. In one such execution, the multicomponent material is present on the bottom of the absorbent structure for immobilizing liquid at the bottom of the absorbent structure. This is beneficial because, by this, liquid is prevented from penetrating through the absorbent structure and approaching at the backsheet of the absorbent article containing the absorbent structure, which provides reduced wet-through leakage. In another execution, the multicomponent material is arranged at the periphery of the absorbent structure, which prevents liquid from running of the absorbent at the sides.

In one embodiment, the absorbent structure according to the present invention is used in the absorbent core of an absorbent article.

The term "absorbent article" is used herein in a very broad sense including any article able to receive and/or absorb and/or contain and/or retain fluids and/or exudates, especially bodily fluids/bodily exudates. In one embodiment, the absorbent article comprises a fluid pervious topsheet, a fluid impervious backsheet that can be water vapour and/or gas pervious, and an absorbent core comprised there between. In one embodiment, the absorbent articles can be disposable absorbent articles. Typical disposable absorbent articles according to the present invention are diapers, surgical and wound dressings and perspiration pads, incontinence pads, and absorbent articles for feminine hygiene like sanitary napkins, panty liners, tampons, interlabial devices or the like.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent structure for use in absorbent articles for personal hygiene, the absorbent structure being provided with multicomponent material,
   wherein the multicomponent material comprises an inert carrier material and chitosan material coated onto the inert carrier material, wherein the inert carrier material is particles; and
   wherein the chitosan material is coated onto the inert carrier material at a thickness of from about 1 to about 100 µm.

2. The absorbent structure of claim 1, wherein the absorbent structure is a fibrous material selected from hydrophilic fibers, hydrophobic fibers or combinations thereof.

3. The absorbent structure of claim 1, wherein the absorbent structure is a foam material.

4. The absorbent structure of claim 1, wherein the chitosan material is acidic, having a pH of from about 3 to about 6.

5. The absorbent structure of claim 4, wherein the chitosan material is a chitosan salt selected from chitosonium pyrrolidone carboxylate, chitosonium lactate or combinations thereof.

6. The absorbent structure of claim 1, wherein the chitosan material is cross-linked.

7. The absorbent structure of claim 1, wherein the inert carrier material is selected from silicon oxide, glass beads, polyethylene granules, polypropylene granules or combinations thereof.

8. The absorbent structure of claim 1, wherein the weight ratio of the inert carrier material to the chitosan material ranges from about 95:5 to about 30:70.

9. The absorbent structure of claim 1, wherein the inert carrier material particles are present as granules having an average diameter ranging from about 50 μm to about 1500 μm; about 100 to about 1000 μm; or about 100 to about 600 μm.

10. The absorbent structure of claim 1, wherein the chitosan material is coated onto the inert carrier material at a thickness of from about 5 to about 30 μm.

11. The absorbent structure of claim 1, wherein the chitosan material is further present in the interior of the inert carrier material.

12. The absorbent structure of claim 1, wherein the chitosan material covers the entire surface of the inert carrier material.

13. The absorbent structure of claim 1, wherein the chitosan material covers not more than about 70% of the surface of the inert carrier material.

14. A disposable absorbent article for personal hygiene comprising an absorbent structure for use in absorbent articles for personal hygiene, the absorbent structure being provided with multicomponent material, wherein the multicomponent material comprises an inert carrier material and chitosan material coated onto the inert carrier material, wherein the inert carrier material is-particles; and wherein the chitosan material is coated onto the inert carrier material at a thickness of from about 1 to about 100 μm.

* * * * *